United States Patent
Dong et al.

(10) Patent No.: US 10,258,661 B2
(45) Date of Patent: Apr. 16, 2019

(54) METHOD FOR EXTRACTING AND REFINING ALKALOIDS FROM IPECAC

(71) Applicant: CHENGDU HERBPURIFY CO., LTD., Chengdu (CN)

(72) Inventors: Weizhen Dong, Chengdu (CN); Jianhong Chang, Chengdu (CN)

(73) Assignee: CHENGDU HERBPURIFY CO., LTD., Chengdu (CN)

( * ) Notice: Subject to any disclaimer, the term of this patent is extended or adjusted under 35 U.S.C. 154(b) by 98 days.

(21) Appl. No.: 15/543,204

(22) PCT Filed: Sep. 23, 2016

(86) PCT No.: PCT/CN2016/099864
§ 371 (c)(1),
(2) Date: Jul. 12, 2017

(87) PCT Pub. No.: WO2017/067366
PCT Pub. Date: Apr. 27, 2017

(65) Prior Publication Data
US 2017/0368126 A1     Dec. 28, 2017

(30) Foreign Application Priority Data
Oct. 22, 2015  (CN) .......................... 2015 1 0697090

(51) Int. Cl.
| | | |
|---|---|---|
| A61K 36/00 | (2006.01) | |
| A61K 36/74 | (2006.01) | |
| C07D 455/08 | (2006.01) | |
| A61K 31/4745 | (2006.01) | |
| A61K 31/706 | (2006.01) | |
| B01D 11/02 | (2006.01) | |
| B01D 15/32 | (2006.01) | |

(52) U.S. Cl.
CPC .......... *A61K 36/74* (2013.01); *A61K 31/4745* (2013.01); *A61K 31/706* (2013.01); *B01D 11/0288* (2013.01); *B01D 15/325* (2013.01); *C07D 455/08* (2013.01); *A61K 2236/15* (2013.01); *A61K 2236/333* (2013.01); *A61K 2236/39* (2013.01); *A61K 2236/51* (2013.01); *A61K 2236/53* (2013.01); *A61K 2236/55* (2013.01)

(58) Field of Classification Search
CPC ...................................................... A61K 36/00
See application file for complete search history.

(56) References Cited

FOREIGN PATENT DOCUMENTS

| | | |
|---|---|---|
| CN | 102633793 | 8/2012 |
| CN | 105384737 | 3/2016 |

OTHER PUBLICATIONS

International Search Report dated Nov. 18, 2016 from application serial No. PCT/CN2016/099864, pp. 4.

*Primary Examiner* — Qiuwen Mi
(74) *Attorney, Agent, or Firm* — Hogan Lovells US LLP

(57) ABSTRACT

Provided is a method for extracting and refining alkaloids from ipecac, comprising: (1) grinding ipecac, adding acidic methanol/ethanol solution for extraction, obtaining an extraction solution A, concentrating under a reduced pressure, and obtaining a concentrated solution B; (2) using reversed-phase polymer filler J for adsorption, and performing desorption by washing with water, collecting a washing solution C, eluting with an alcoholic solution E and collecting a desorption solution D; (3) injecting the washing solution C and the desorption solution D into a preparative high performance liquid chromatograph for separation and purification respectively, to collect a solution G, and a solution H and a solution I respectively; and (4) concentrating the solutions G, H and I, which are then subjected to reversed-phase polymer filler K for adsorption respectively; eluting them respectively after adsorption with an alcoholic solution F; concentrating obtained eluates to dryness; and then performing vacuum drying.

10 Claims, No Drawings

METHOD FOR EXTRACTING AND REFINING ALKALOIDS FROM IPECAC

TECHNICAL FIELD

The present invention relates to the technical field of extraction of Chinese herbal medicine ingredients, and particularly to a method for extracting and refining alkaloids from ipecac.

BACKGROUND ART

Ipecac, which is dried rhizome of *Cephaelis ipecacuanha* (Brot.) A. Rich or *Cephaelis acuminate* Karsten of Rubiaceae plants is a medicinal material imported from Brazil, Costa Rica or India and is recorded in United States Pharmacopeia, Japanese Pharmacopoeia and European Pharmacopoeia. Researches on modern pharmacology indicated that ipecac has effects of relieving cough and reducing sputum, inducing vomiting, resisting amoebiasis and the like. There are certain researches which showed that the main pharmacologically active ingredients of ipecac are chemical ingredients like alkaloids. Among them, emetine and cephaeline are dominant, which account for more than 90% of the total alkaloids. As emetine and cephaeline are free and unstable, hydrochlorides of them are usually used for treatment in clinical practice. Emetine hydrochloride is usually used to treat acute amoebiasis, and cephaeline hydrochloride is mainly used to induce vomiting and reduce sputum. Among total alkaloids of ipecac, there is still another alkaloid having an English name AIDS031406, with a CAS number of 15401-60-2 and a chemical formula of $C_{27}H_{35}NO_{12}$, and it has no Chinese name yet. There is little research about it in China and abroad, and at present, there is only a commercially available product with a trade name of Ipecoside for laboratory content determination, control tests and pharmacological tests.

Although various alkaloids of ipecac, such as emetine and cephaeline, are structurally similar to each other, they are significantly different in absorption, distribution, metabolization and excretion in a human body and the alkaloids are, in a certain extent, different in pharmacology, too. In order to make drug use safer and more accurate, it is necessary to separate, purify and refine various alkaloids in the ipecac. However, as ipecac is an imported medicinal material, there is very little research about it in China, and correspondingly there are few documents regarding methods for extracting, separating and refining alkaloids from ipecac. A few foreign documents describe researched methods for extracting and separating emetine, cephaeline and AIDS031406 in ipecac. Patent CN102633793A discloses a preparation method for extracting and separating emetine hydrochloride and cephaeline hydrochloride from ipecac, which is performed through the steps of ultrasonic extraction, concentration, extraction separation and purification, and freeze drying. The method is able to obtain emetine hydrochloride and cephaeline hydrochloride with a purity of more than 98%. However, this preparation method is a semi-preparation method, in which the employed reagents and equipment are all used for laboratory analyses. The method has a low yield and output, restricting its use to laboratory studies and rendering it unsuitable for use in industrial production. In addition, a diethyl ether reagent is used during an extraction process. Diethyl ether is an anesthetic reagent which is highly volatile, and its use and dosage is under strict control. Thus, it cannot be applied to production at all.

SUMMARY

In view of the above, a method is disclosed for extracting and refining alkaloids from ipecac. The method can be used to extract and separate emetine and cephaeline and AIDS031406 in the form of hydrochloride from ipecac, with purity of emetine hydrochloride reaching 98.5% or more, purity of cephaeline hydrochloride reaching 98.5% or more, and purity of AIDS031406 hydrochloride reaching 99%. The method achieves a total yield of 80% or more, has a high output, and is suitable for industrial production. It is a simple method which results in high purity. And it is environment friendly as no other organic solvents are used in the process except methanol or ethanol.

In order to solve the above technical problems, the technical solution provided by the present invention is embodied as a method for extracting and refining alkaloids from ipecac, the method including the steps of:
1) extraction and concentration: grinding a medicinal material of ipecac, adding acidic methanol solution or acidic ethanol solution for extraction to give an extraction solution A, and concentrating the extraction solution A under a reduced pressure to give a concentrated solution B, wherein the purpose of adding the acidic methanol solution or acidic ethanol solution is to convert the emetine, cephaeline and AIDS031406 in the ipecac into a stable hydrochloride form;
2) separation and enrichment: subjecting the concentrated solution B to a reversed-phase polymer filler J for adsorption, and performing desorption after the adsorption is completed, wherein water washing is performed, a washing solution C is collected, then eluting is performed with an alcoholic solution E, and a desorption solution D is collected, wherein the washing solution C contains cephaeline hydrochloride, and the desorption solution D contains emetine hydrochloride and AIDS031406 hydrochloride;
3) purification: injecting the washing solution C into a preparative high performance liquid chromatograph for separation and purification, and collecting a solution G according to the corresponding spectrum band in the detection chromatogram of the cephaeline hydrochloride; and injecting the desorption solution D into the preparative high performance liquid chromatograph for separation and purification, and collecting a solution H and a solution I according to corresponding spectrum bands in the detection chromatograms of the emetine hydrochloride and AIDS031406 hydrochloride, respectively, wherein pure solutions containing the three ingredients are obtained directly by the preparative high performance liquid chromatograph, which improves the yield; and
4) enrichment and drying: concentrating the solution G, solution H and solution I, which are then subjected to a reversed-phase polymer filler K for adsorption respectively; after the adsorption is completed, eluting them respectively with an alcoholic solution F; concentrating eluates obtained after eluting under a reduced pressure to dryness; and then vacuum drying to obtain pure cephaeline hydrochloride, pure emetine hydrochloride, and pure AIDS031406 hydrochloride.

Preferably, in Step (1), the acidic methanol solution or acidic ethanol solution contains 0.05% by volume of hydrochloric acid and 70-90% by volume of methanol or ethanol.

More preferably, the acidic methanol solution or acidic ethanol solution contains 80% methanol or ethanol by volume.

Preferably, in Step (1), the extraction solution A is concentrated under a reduced pressure at a temperature not higher than 65° C.

Preferably, in Step (2), the reversed-phase polymer filler J is any one selected from the group comprising AB-8-type macroporous adsorption resin, D101-type macroporous adsorption resin, XAD-16N filler, MCIGEL polymer filler, YMC filler, and NM100-reversed-phase polymer chromatographic filler. More preferably, in Step (2), the reversed-phase polymer filler J is any one selected from the group comprising AB-8-type macroporous adsorption resin, D101-type macroporous resin, and NM100-reversed-phase polymer chromatographic filler.

Preferably, in Step (2), the alcoholic solution E is a methanol solution or ethanol solution, and in the alcoholic solution E, the methanol or ethanol has a volume percentage of 30-80%.

Preferably, in Step (4), the reversed-phase polymer filler K is embodied as AB-8-type macroporous adsorption resin.

Preferably, in Step (4), the alcoholic solution F is a methanol solution or ethanol solution, and in the alcoholic solution F, the methanol or ethanol has a volume percentage of 80-100%.

Preferably, in Step (4), the concentration under a reduced pressure is performed at a temperature not higher than 55° C., and the vacuum drying is performed at a temperature of 40-50° C.

The AB-8-type macroporous adsorption resin, the D101-type macroporous adsorption resin, the XAD-16N filler, the MCIGEL polymer filler, the YMC filler, and the NM100-reversed-phase polymer chromatographic filler are all commercially available products.

The technical solution of the present invention provides a method for extracting and refining alkaloids from ipecac, including the operation steps of extraction and concentration, separation and enrichment, purification, and enrichment and drying. In the step of extraction and concentration, acidic methanol solution or acidic ethanol solution is used for extraction, to convert the emetine, cephaeline and AIDS031406 in the ipecac into a stable hydrochloride form, facilitating processing of subsequent steps and increasing the purity of products. In the step of separation and enrichment, the reversed-phase polymer filler is used for enrichment so as to separate the cephaeline hydrochloride, emetine hydrochloride and AIDS031406 hydrochloride. Here, the washing solution C contains cephaeline hydrochloride; the desorption solution D contains the emetine hydrochloride and AIDS031406 hydrochloride; and use of organic solvents other than methanol or ethanol is avoided. In the step of purification, pure solutions containing three ingredients are obtained directly by a preparative high performance liquid chromatograph, improving the yield. In the step of enrichment and drying, the pure solutions are converted into a solid form through another enrichment, which is then subjected to vacuum drying to give separated pure cephaeline hydrochloride, pure emetine hydrochloride, and pure AIDS031406 hydrochloride.

As verified by experiments using the method, the purity of the emetine hydrochloride may reach 98.5% or more, the purity of cephaeline hydrochloride may reach 98.5% or more, the purity of AIDS031406 hydrochloride may reach 99%, and the total yield may reach 80-90%. Compared with the prior art in which the purity reaches 95% and the yield is only 30%, the technical solution of the present invention obtains ingredients with high purities, and provides an obvious advantage in terms of yield. In addition, the method is simple. No organic solvents will be used in the process other than methanol or ethanol, which is environment friendly. The method may be used for refined preparation of standard products, and it may also be used for industrialized production. The method provides a stable and controllable quality, and thus has potential for widespread application.

DETAILED DESCRIPTION

In order to enable those skilled in the art to better understand the technical solution of the present invention, below the present invention will be described in detail in conjunction with various embodiments.

In a first embodiment, the method for extracting and refining alkaloids from ipecac includes the following steps of:

1) extraction and concentration: grinding a medicinal material of ipecac that is native to Costa Rica, adding acidic methanol solution or acidic ethanol solution for extraction for 6 times and combining to obtain an extraction solution A; and concentrating the extraction solution A under a reduced pressure at 60° C. to obtain a concentrated solution B;

2) separation and enrichment: subjecting the concentrated solution B to a D101-type macroporous adsorption resin for adsorption; and performing desorption after the adsorption is completed, wherein water washing is performed, a washing solution C is collected, then eluting is performed with an alcoholic solution E with a concentration of 45-60% and a desorption solution D is collected, wherein the alcoholic solution E is methanol solution;

3) separation and purification; injecting the washing solution C into a preparative high performance liquid chromatograph for separation and purification, and collecting a solution G according to the corresponding spectrum band in the detection chromatogram of the cephaeline hydrochloride; and injecting the desorption solution D into the preparative high performance liquid chromatograph for separation and purification, and collecting a solution H and a solution I according to corresponding spectrum bands in the detection chromatograms of the emetine hydrochloride and AIDS031406 hydrochloride, respectively; and 4) enrichment and drying: concentrating the solution G, solution H and solution I, which are then subjected to AB-8-type macroporous adsorption resin for adsorption respectively; eluting, after the adsorption is completed, the solutions respectively with an alcoholic solution F with a concentration of 95-100%, the alcoholic solution F being methanol or ethanol solution; concentrating eluates, obtained after eluting, under a reduced pressure at 50° C. to dryness; and then performing vacuum drying at 45° C. to obtain pure cephaeline hydrochloride, pure emetine hydrochloride, and pure AIDS031406 hydrochloride.

In the above, in Step (1), the ipecac was separated into six groups and the extraction for each group was performed according to different volume percentages of methanol or ethanol in the acidic methanol solution or acidic ethanol solution:

Group 1 was treated with an acidic methanol solution in which the methanol had a volume percentage of 70%.

Group 2 was treated with an acidic methanol solution in which the methanol had a volume percentage of 80%.

Group 3 was treated with an acidic methanol solution in which the methanol had a percentage volume of 90%.

Group 4 was treated with an acidic ethanol solution in which the ethanol had a volume percentage of 70%.

Group 5 was treated with an acidic ethanol solution in which the ethanol had a volume percentage of 80%.

Group 6 was treated with an acidic ethanol solution in which the ethanol had a volume percentage of 90%.

In each of the above groups, the acidity was provided by hydrochloric acid that had a volume percentage of 0.05%. High-performance liquid chromatography (HPLC) was used to detect purities of the resultant pure cephaeline hydrochloride, pure emetine hydrochloride, and pure AIDS031406 hydrochloride and the yield of the total alkaloids from each group respectively. See Table 1 for the group detection results.

TABLE 1

Group Detection Results in Embodiment 1

| Group | Purity (%) Cephaeline hydrochloride | Emetine hydrochloride | AIDS031406 hydrochloride | Total yield (%) |
|---|---|---|---|---|
| 1 | 99.23% | 99.5% | 99.4% | 81% |
| 2 | 99.6% | 99.59% | 99.58% | 90% |
| 3 | 98.96% | 98.8% | 99.21% | 84% |
| 4 | 98.59% | 98.55% | 98.89% | 85% |
| 5 | 98.95% | 99.2% | 99.3% | 88% |
| 6 | 99.13% | 99.23% | 99.1% | 80% |

As seen from Table 1 above, among Groups 1 to 6, each ingredient has a relatively high purity of 98% or more. In addition to the high purity, the yield can reach at least 80%. Group 2, which was treated with the acidic methanol solution in which the methanol had a volume percentage of 80%, provides the best effect and is thus a preferable solution of the first embodiment.

In a second embodiment, the method for extracting and refining alkaloids from ipecac includes the following steps of:

1) extraction and concentration: grinding a medicinal material of ipecac that is native to Costa Rica, and adding acidic methanol solution for extraction for 6 times, the acidic methanol solution containing 0.05% by volume of hydrochloric acid and 80% by volume of methanol; combining to obtain an extraction solution A; and concentrating the extraction solution A under a reduced pressure at 60° C. to obtain a concentrated solution B;

2) separation and enrichment: subjecting the concentrated solution B to a reversed-phase polymer filler J for adsorption; and performing desorption after the adsorption is completed, wherein water washing is performed, a washing solution C is collected, then eluting is performed with an alcoholic solution E with a concentration of 45-60% and a desorption solution D is collected, wherein the alcoholic solution E is methanol or ethanol solution;

3) separation and purification: injecting the washing solution C into a preparative high performance liquid chromatograph for separation and purification, and collecting a solution G according to the corresponding spectrum band in the detection chromatogram of the cephaeline hydrochloride; and injecting the desorption solution D into the preparative high performance liquid chromatograph for separation and purification, and collecting a solution H and a solution I according to corresponding spectrum bands in the detection chromatograms of the emetine hydrochloride and AIDS031406 hydrochloride, respectively; and 4) enrichment and drying: concentrating the solution G, solution H and solution I, which are then subjected to AB-8-type macroporous adsorption resin for adsorption respectively; eluting, after the adsorption is completed, the solutions respectively with an alcoholic solution F with a concentration of 95-100%, the alcoholic solution F being methanol or ethanol solution; concentrating eluates, obtained after eluting, under a reduced pressure at 50° C. to dryness; and then performing vacuum drying at 45° C. to obtain pure cephaeline hydrochloride, pure emetine hydrochloride, and pure AIDS031406 hydrochloride.

In the above, in Step (2), the concentrated solution B was separated into six groups and the adsorption for each group was performed according to different types of reversed-phase polymer filler J selected:

Group A used AB-8-type macroporous adsorption resin.
Group B used D101-type macroporous adsorption resin.
Group C used XAD-16N filler.
Group D used MCIGEL polymer filler.
Group E used YMC filler.
Group F used NM100-reversed-phase polymer chromatographic filler.

HPLC was used to detect purities of the resultant pure cephaeline hydrochloride, pure emetine hydrochloride and pure AIDS031406 hydrochloride, and the yield of the total alkaloids from each group respectively. See Table 2 for the group detection results.

TABLE 2

Group Detection Results in Embodiment 2

| Group | Purity (%) Cephaeline hydrochloride | Emetine hydrochloride | AIDS031406 hydrochloride | Total yield (%) |
|---|---|---|---|---|
| A | 99.6% | 99.5% | 99.52% | 90% |
| B | 99.55% | 99.51% | 99.5% | 90% |
| C | 99.12% | 99.12% | 99.5% | 86% |
| D | 98.95% | 98.89% | 98.92% | 85% |
| E | 99.23% | 99.13% | 99.21% | 89% |
| F | 99.58% | 99.59% | 99.49% | 90% |

As seen from Table 2 above, the fillers used by Groups A, B and F provide good purity and yield data. Therefore, it is a preferable solution of the second embodiment to use AB-8-type macroporous adsorption resin, D101-type macroporous resin, or NM100-reversed-phase polymer chromatographic filler for separation and purification.

In a third embodiment, the method for extracting and refining alkaloids from ipecac includes the following steps of:

1) extraction and concentration: grinding a medicinal material of ipecac that is native to Costa Rica, and adding thereto acidic methanol solution for extraction for 6 times, the acidic methanol solution containing 0.05% by volume of hydrochloric acid and 80% by volume of methanol; combining to obtain an extraction solution A; and concentrating the extraction solution A under a reduced pressure at 60° C. to obtain a concentrated solution B;

2) separation and enrichment: subjecting the concentrated solution B to an AB-8-type macroporous adsorption resin for adsorption; and performing desorption after the adsorption is completed, wherein water washing is performed, a washing solution C is collected, then eluting is performed with an alcoholic solution E and a desorption solution D is collected;

3) separation and purification: injecting the washing solution C into a preparative high performance liquid chromatograph for separation and purification, and collecting a solution G according to the corresponding spectrum band in the detection chromatogram of the cephaeline hydrochloride; and injecting the desorption solution D into the preparative high performance liquid chromatograph for separation and purification, and collecting a solution H and a solution I according to corresponding spectrum bands in the detection chromatograms of the emetine hydrochloride and AIDS031406 hydrochloride, respectively; and 4) enrichment and drying: concentrating the solution G, solution H and solution I, which are then subjected to AB-8-type macroporous adsorption resin for adsorption respectively; eluting, after the adsorption is completed, the solutions respectively with an alcoholic solution F with a concentration of 95-100%, the alcoholic solution F being methanol or ethanol solution; concentrating eluates, obtained after eluting, under a reduced pressure at 50° C. to dryness; and then performing vacuum drying at 45° C. to obtain pure cephaeline hydrochloride, pure emetine hydrochloride, and pure AIDS031406 hydrochloride.

In the above, in Step (2), the eluting was separated into eight groups and the eluting for each group was performed according to different types and volume percentages of alcohol in the alcoholic solution E:

Group G was treated with a methanol solution with a volume percentage of 30-45%.

Group H was treated with a methanol solution with a volume percentage of 45-60%.

Group I was treated with a methanol solution with a volume percentage of 60-70%.

Group J was treated with a methanol solution with a volume percentage of 70-80%.

Group K was treated with an ethanol solution with a volume percentage of 30-45%.

Group L was treated with an ethanol solution with a volume percentage of 45-60%.

Group M was treated with an ethanol solution with a volume percentage of 60-70%.

Group N was treated with an ethanol solution with a volume percentage of 70-80%.

HPLC was used to detect purities of the resultant pure cephaeline hydrochloride, pure emetine hydrochloride, and pure AIDS031406 hydrochloride, and the yield of the total alkaloids from each group respectively. See Table 3 for the group detection results.

TABLE 3

Group Detection Results in Embodiment 3

| Group | Purity (%) Cephaeline hydrochloride | Emetine hydrochloride | AIDS031406 hydrochloride | Total yield (%) |
|---|---|---|---|---|
| G | 99.24% | 99.36% | 99.53% | 80% |
| H | 99.45% | 99.53% | 99.5% | 90% |
| I | 99.32% | 99.23% | 99.21% | 82% |
| J | 98.6% | 98.8% | 99.5% | 83% |
| K | 99.5% | 99.2% | 99.3% | 85% |
| L | 99.55% | 99.5% | 99.51% | 90% |
| M | 98.92% | 98.46% | 99.2% | 86% |
| N | 98.9% | 98.8% | 99.0% | 82% |

As seen from Table 3 above, using either methanol or ethanol provides a high purity and yield. Among these groups, Groups H and L provide better purity and yield. Namely, when the methanol or ethanol has a volume percentage of 45-60%, they provide the best effect and thus they are a preferable solution of the third embodiment.

In a fourth embodiment, the method for extracting and refining alkaloids from ipecac includes the following steps of:

1) extraction and concentration: grinding a medicinal material of ipecac that is native to Costa Rica, and adding acidic methanol solution for extraction for 6 times, the acidic methanol solution containing 0.05% by volume of hydrochloric acid and 80% by volume of methanol; combining to obtain an extraction solution A; and concentrating the extraction solution A under a reduced pressure at 60° C. to obtain a concentrated solution B;

2) separation and enrichment: subjecting the concentrated solution B to an NM100-reversed-phase polymer chromatographic filler for adsorption; and performing desorption after the adsorption is completed, wherein water washing is performed, a washing solution C is collected, then eluting is performed with an alcoholic solution E with a concentration of 45-60%, and a desorption solution D is collected, wherein the alcoholic solution E is methanol solution;

3) separation and purification: injecting the washing solution C into a preparative high performance liquid chromatograph for separation and purification, and collecting a solution G according to the corresponding spectrum band in the detection chromatogram of the cephaeline hydrochloride; and injecting the desorption solution D into the preparative high performance liquid chromatograph for separation and purification, and collecting a solution H and a solution I according to the corresponding spectrum bands in the detection chromatograms of the emetine hydrochloride and AIDS031406 hydrochloride, respectively; and 4) enrichment and drying: concentrating the solution G, solution H and solution I, which are then subjected to AB-8-type macroporous adsorption resin for adsorption respectively; eluting, after the adsorption is completed, the solutions respectively with an alcoholic solution F; concentrating eluates, obtained after eluting, under a reduced pressure at 50° C. to dryness; then performing vacuum drying at 45° C. to obtain pure cephaeline hydrochloride, pure emetine hydrochloride, and pure AIDS031406 hydrochloride In the above, in Step (4), the eluting was separated into eight groups and the eluting for each group performed according to different types of and volume percentages of alcohol of the alcoholic solution F:

Group I was treated with a methanol solution with a volume percentage of 80-85%.

Group II was treated with a methanol solution with a volume percentage of 85-90%.

Group III was treated with a methanol solution with a volume percentage of 90-95%.

Group IV was treated with a methanol solution with a volume percentage of 95-100%.

Group V was treated with an ethanol solution with a volume percentage of 80-85%.

Group VI was treated with an ethanol solution with a volume percentage of 85-90%.

Group VII was treated with an ethanol solution with a volume percentage of 90-95%.

Group VIII was treated with an ethanol solution with a volume percentage of 95-100%.

HPLC was used to detect purities of the resultant pure cephaeline hydrochloride, pure emetine hydrochloride and pure AIDS031406 hydrochloride, and the yield of the total alkaloids from each group respectively. See Table 4 for the group detection results.

TABLE 4

Group Detection Results in Embodiment 4

| Group | Purity (%) Cephaeline hydrochloride | Emetine hydrochloride | AIDS031406 hydrochloride | Total yield (%) |
|---|---|---|---|---|
| I | 99.41% | 99.14% | 99.18% | 80% |
| II | 98.9% | 99.3% | 99.2% | 85% |
| III | 99.16% | 99.24% | 99.12% | 88% |
| IV | 99.48% | 99.5% | 99.4% | 90% |
| V | 99.2% | 99.3% | 99.4% | 84% |
| VI | 99.0% | 98.8% | 99.3% | 85% |
| VII | 98.7% | 98.9% | 99.1% | 82% |
| VIII | 99.52% | 99.53% | 99.48% | 90% |

As seen from Table 4 above, each ingredient has a relatively high purity and yield in Group IV and Group VIII. Therefore, using methanol or ethanol with a volume percentage of 95-100% provides the best effect and the highest yield and is thus a preferable solution of the fourth embodiment.

While certain exemplary embodiments have been described, it is to be understood that such embodiments are merely illustrative of and not restrictive on the broad invention, and that this invention is not limited to the specific embodiments shown and described, since various other modifications may occur to those ordinarily skilled in the art. The scope of protection of the present invention is defined by the Claims. For a person ordinarily skilled in the art, some improvements and modifications may be made without departing from the spirit and scope of the present invention, and such improvements and modifications should also be included within the scope of protection of the present invention.

The invention claimed is:

1. A method for extracting and refining alkaloids from ipecac, the method comprising steps of:
   (1) extraction and concentration: grinding medicinal material of ipecac, and adding an acidic methanol solution or an acidic ethanol solution for extraction to give an extraction solution A; and concentrating the extraction solution A under a reduced pressure to give a concentrated solution B;
   (2) separation and enrichment: subjecting the concentrated solution B to a reversed-phase polymer filler J for adsorption; and performing desorption after the adsorption is completed, wherein water washing is performed, a washing solution C is collected, then eluting is performed with an alcoholic solution E, and a desorption solution D is collected;
   (3) purification: injecting the washing solution C into a preparative high performance liquid chromatograph for separation and purification, and collecting a solution G according to a corresponding spectrum band in a detection chromatogram of cephaeline hydrochloride; and injecting the desorption solution D into the preparative high performance liquid chromatograph for separation and purification, and collecting a solution H and a solution I according to corresponding spectrum bands in detection chromatograms of emetine hydrochloride and AIDS031406 hydrochloride, respectively; and
   (4) enrichment and drying: concentrating the solution G, solution H and solution I, which are then subjected to a reversed-phase polymer filler K for adsorption respectively; eluting, after the adsorption is completed, the solutions respectively with an alcoholic solution F; concentrating eluates, obtained after eluting, under a reduced pressure to dryness; and then performing vacuum drying to obtain pure cephaeline hydrochloride, pure emetine hydrochloride and pure AIDS031406 hydrochloride.

2. The method according to claim 1, wherein in Step (1), the acidic methanol solution or acidic ethanol solution contains 0.05% by volume of hydrochloric acid and 70-90% by volume of methanol or ethanol.

3. The method according to claim 2, wherein the acidic methanol solution or acidic ethanol solution contains 80% methanol or ethanol by volume.

4. The method according to claim 1, wherein in Step (1), the extraction solution A is concentrated under a reduced pressure at a temperature not higher than 65° C.

5. The method according to claim 1, wherein in Step (2), the reversed-phase polymer filler J comprises AB-8-type macroporous adsorption resin, D101-type macroporous adsorption resin, XAD-16N filler, MCIGEL polymer filler, YMC filler or NM100-reversed-phase polymer chromatographic filler.

6. The method according to claim 5, wherein in Step (2), the reversed-phase polymer filler J comprises AB-8-type macroporous adsorption resin, D101-type macroporous resin or NM100-reversed-phase polymer chromatographic filler.

7. The method according to claim 1, wherein in Step (2), the alcoholic solution E is a methanol solution or an ethanol solution, and the alcoholic solution E contains 30-80% methanol or ethanol by volume.

8. The method according to claim 1, wherein in Step (4), the reversed-phase polymer filler K comprises AB-8-type macroporous adsorption resin.

9. The method according to claim 1, wherein in Step (4), the alcoholic solution F is a methanol solution or an ethanol solution, and the alcoholic solution F contains 80-100% methanol or ethanol by volume.

10. The method according to claim 1, wherein in Step (4), said concentrating under a reduced pressure is performed at a temperature not higher than 55° C., and the vacuum drying is performed at a temperature of 40-50° C.

* * * * *